United States Patent
Ford et al.

(10) Patent No.: US 8,758,340 B2
(45) Date of Patent: Jun. 24, 2014

(54) APPLICATOR SYSTEM FOR DEPLOYING ELECTRODES

(75) Inventors: John H. Ford, San Jose, CA (US); Scott H. West, Livermore, CA (US); John W. Gaiser, Mountain View, CA (US); Patrick J. Rimroth, San Jose, CA (US)

(73) Assignee: Mederi Therapeutics, Inc., Norwalk, CT (US)

( * ) Notice: Subject to any disclaimer, the term of this patent is extended or adjusted under 35 U.S.C. 154(b) by 876 days.

(21) Appl. No.: 12/287,404

(22) Filed: Oct. 9, 2008

(65) Prior Publication Data

US 2009/0043302 A1    Feb. 12, 2009

Related U.S. Application Data

(63) Continuation of application No. 11/145,743, filed on Jun. 6, 2005, now abandoned.

(60) Provisional application No. 60/581,396, filed on Jun. 21, 2004.

(51) Int. Cl.
*A61B 18/14* (2006.01)
*A61B 18/00* (2006.01)

(52) U.S. Cl.
CPC ... *A61B 18/1477* (2013.01); *A61B 2018/00267* (2013.01)
USPC .......................................................... 606/41

(58) Field of Classification Search
CPC ................. A61B 18/1492; A61B 2018/00267; A61B 2018/1425; A61B 2018/1475; A61B 18/14; A61B 18/1477
USPC .................... 606/41, 45, 46, 48–52, 205–207
See application file for complete search history.

(56) References Cited

U.S. PATENT DOCUMENTS

| | | | |
|---|---|---|---|
| 5,478,350 A | 12/1995 | Kratsch et al. | |
| 5,782,844 A | 7/1998 | Yoon et al. | |
| 5,807,393 A | 9/1998 | Williamson et al. | |
| 5,980,519 A | 11/1999 | Hahnen et al. | |
| 6,221,071 B1 | 4/2001 | Sherry et al. | |
| 6,254,598 B1 * | 7/2001 | Edwards et al. | 606/41 |
| 6,645,201 B1 | 11/2003 | Utley et al. | |
| 6,923,806 B2 | 8/2005 | Hooven et al. | |
| 7,335,197 B2 | 2/2008 | Sage et al. | |
| 2005/0033271 A1 | 2/2005 | Qin et al. | |
| 2005/0049660 A1 | 3/2005 | Croft | |
| 2005/0070978 A1 | 3/2005 | Bek et al. | |
| 2005/0228371 A1 | 10/2005 | West et al. | |
| 2005/0288664 A1 | 12/2005 | Ford et al. | |
| 2006/0089636 A1 | 4/2006 | Christopherson et al. | |
| 2006/0224157 A1 | 10/2006 | Utley et al. | |
| 2007/0118108 A1 | 5/2007 | Croft | |
| 2008/0103498 A1 | 5/2008 | West et al. | |
| 2011/0112529 A1 | 5/2011 | Shikhman | |

* cited by examiner

*Primary Examiner* — Nathan R Price

(57) ABSTRACT

Systems and methods deploy an electrode from a catheter assembly. The systems and methods provide a catheter handle having a trigger lever adapted to carry an actuator rod. The actuator rod is adapted to cause movement of the electrode between a retracted position and an extended position. A pinion is carried by the trigger lever for engagement with a rack carried by the actuator rod. Compression of the trigger lever moves the rack along the actuator rod between a first position corresponding to the electrodes being in the retracted position and a second position corresponding to either the primed electrode firing position or the electrodes being in an extended position.

24 Claims, 16 Drawing Sheets

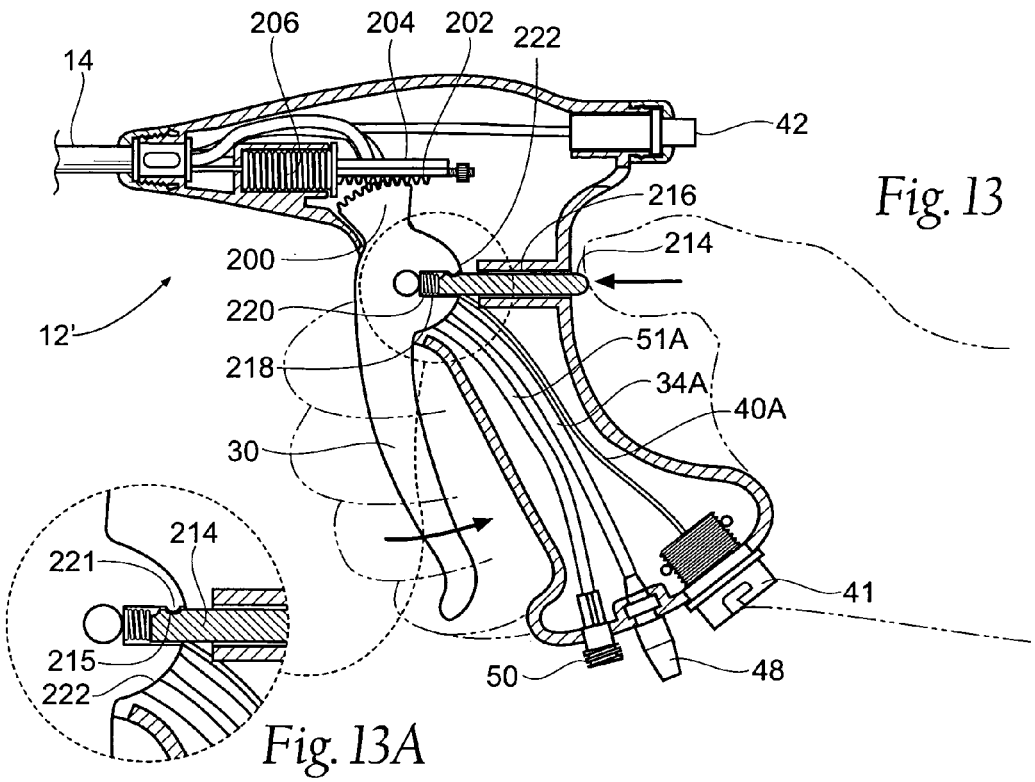
Fig. 13
Fig. 13A
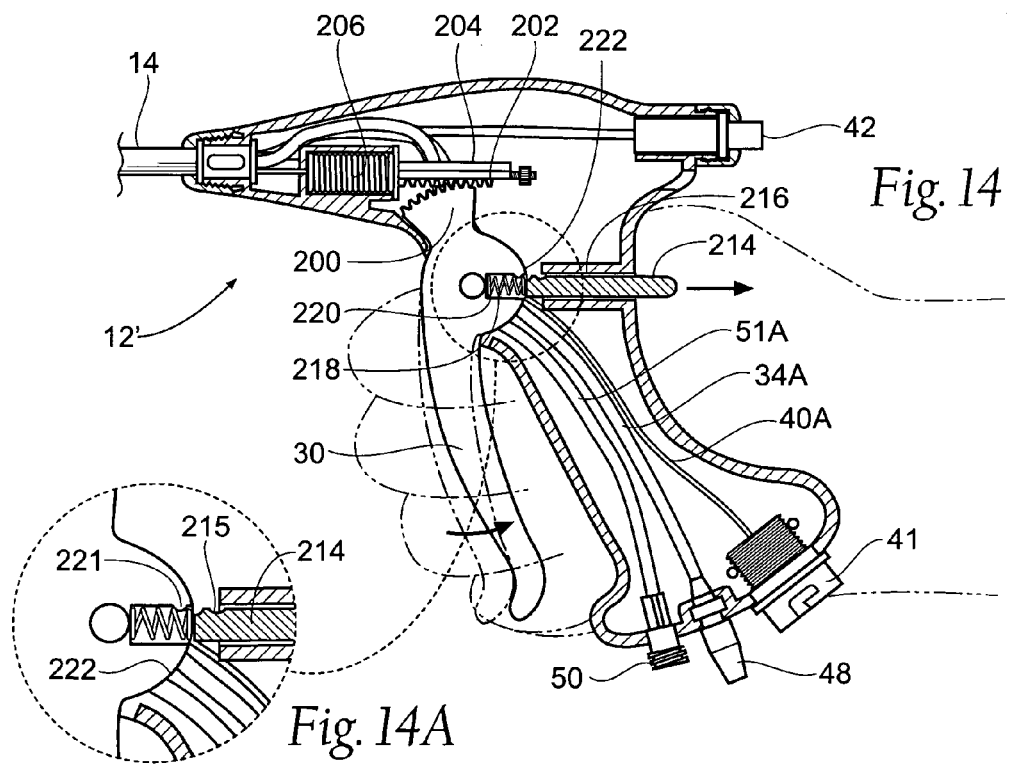
Fig. 14
Fig. 14A

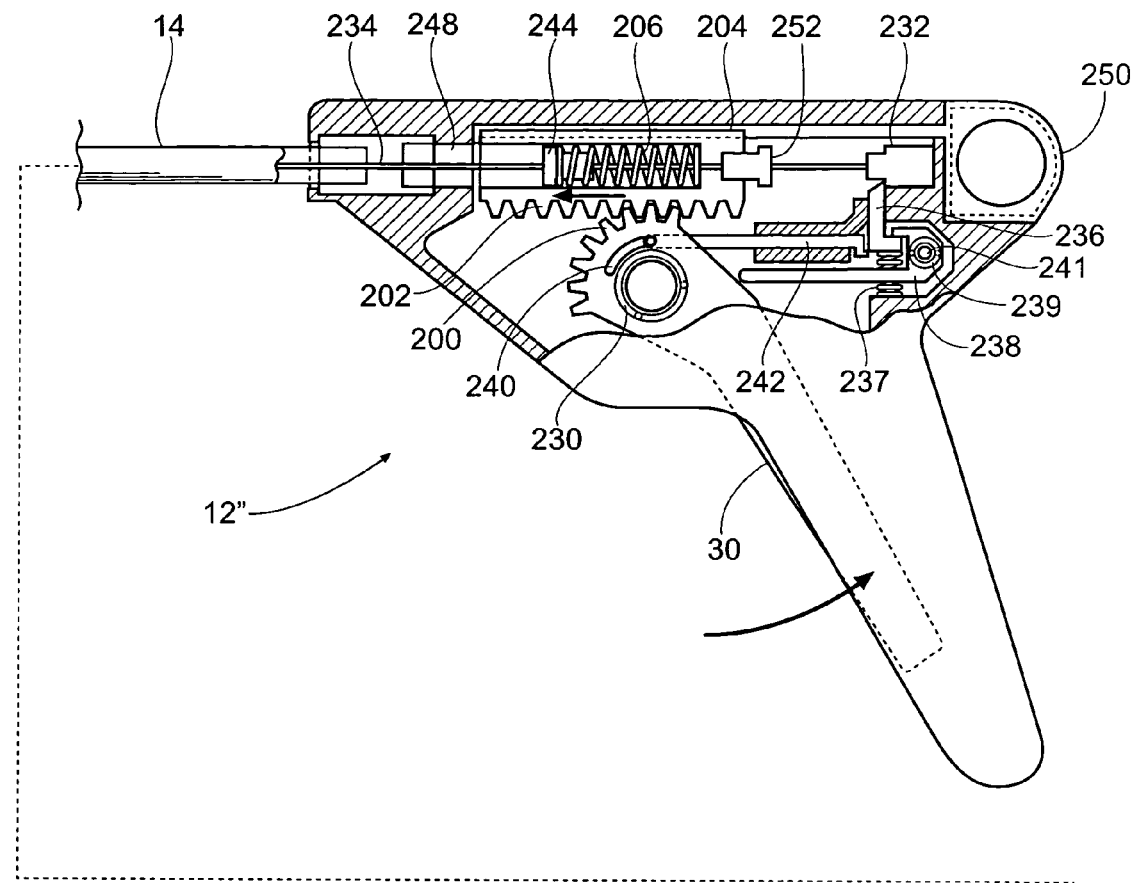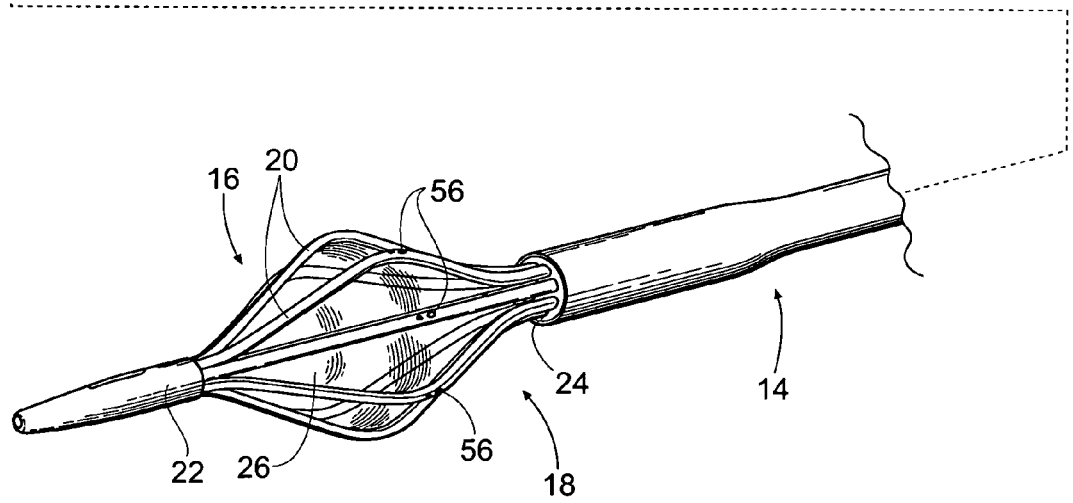
Fig. 17

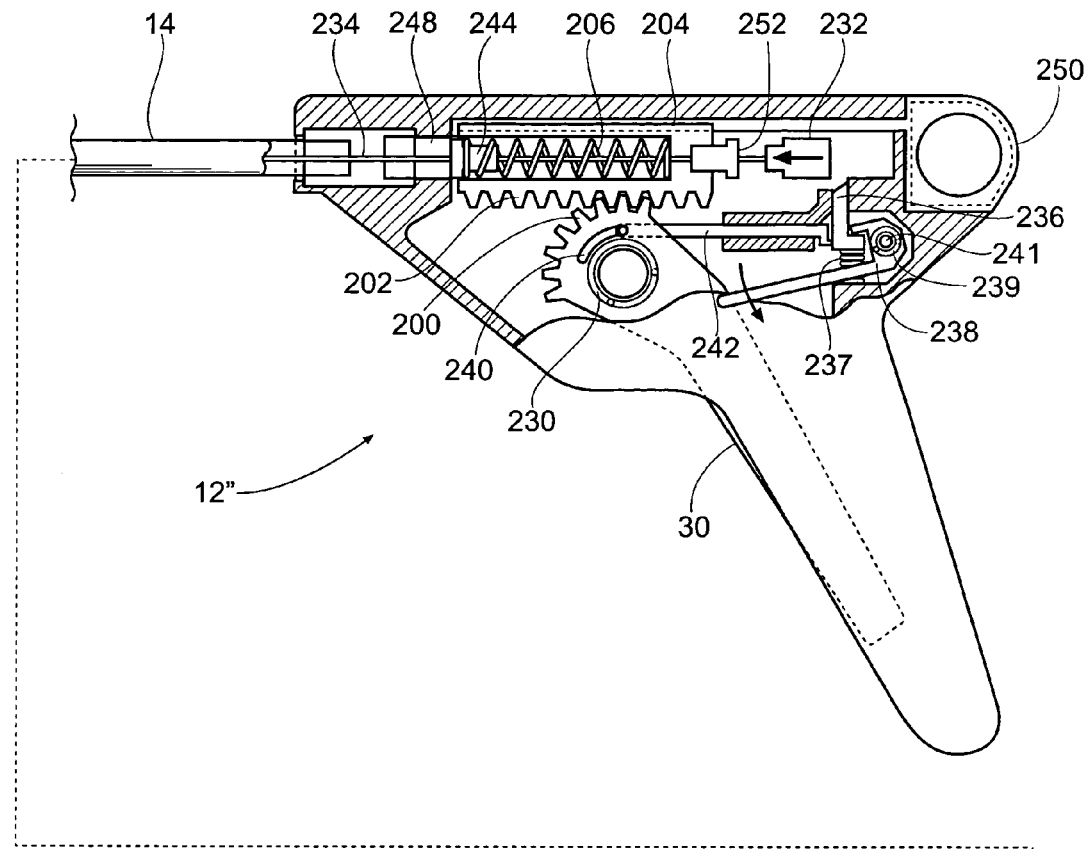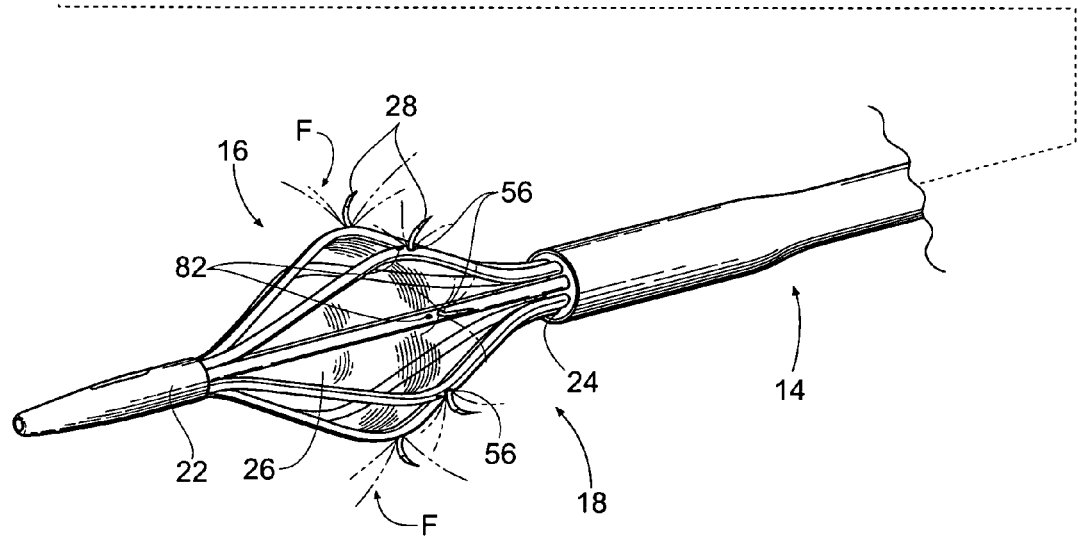
Fig. 18

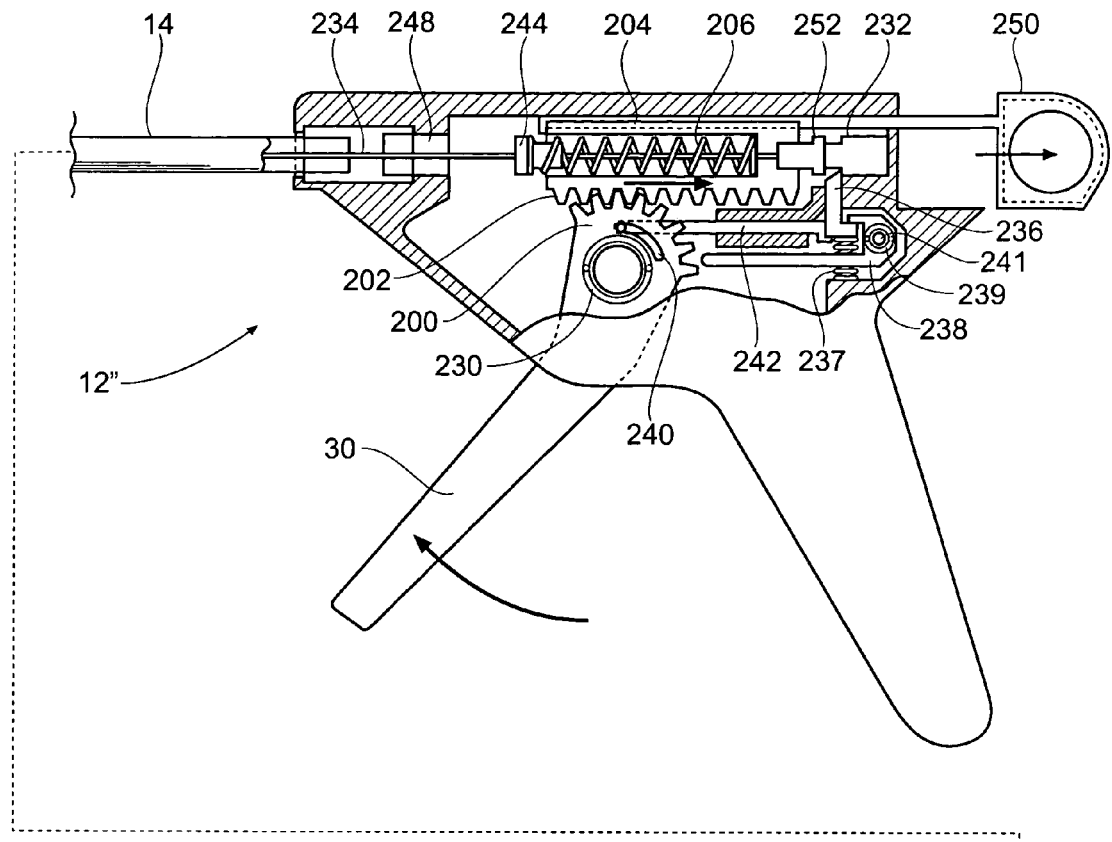
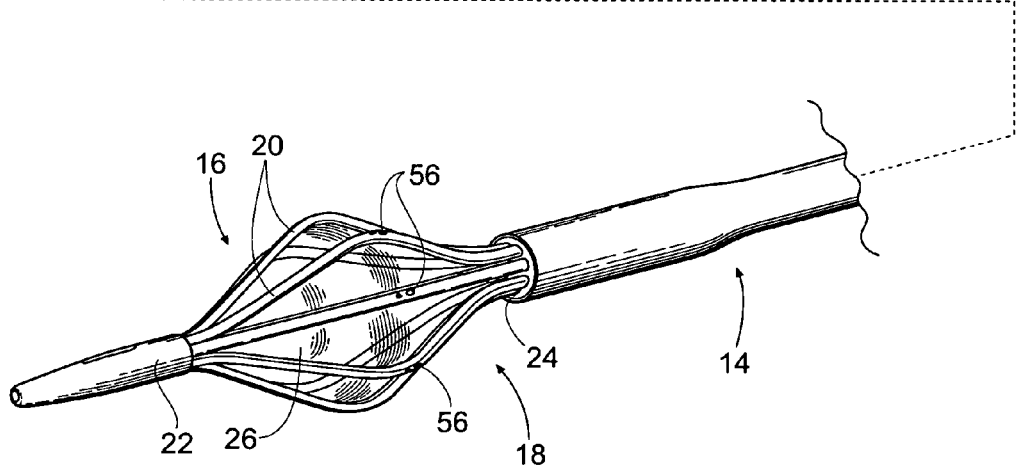
Fig. 19

APPLICATOR SYSTEM FOR DEPLOYING ELECTRODES

RELATED APPLICATION

This is a continuation application which claims the benefit of U.S. patent application Ser. No. 11/145,743, filed Jun. 6, 2005, now abandoned and entitled "Systems and Methods for Treating Tissue Regions of the Body" which claims the benefit of U.S. Provisional Patent Application Ser. No. 60/581,396, filed Jun. 21, 2004, and entitled "Systems and Methods for Treating Tissue Regions of the Body" which are incorporated herein by reference.

FIELD OF THE INVENTION

The invention is directed to devices, systems and methods for treating tissue regions of the body.

BACKGROUND OF THE INVENTION

Catheter-based devices that deploy expandable structures into interior body regions are well known. These structures are typically introduced through a body lumen or vessel in a collapsed, low profile condition. Once at or near the targeted body region, the structures are expanded in situ into an enlarged condition to make contact with tissue. The structures can carry operative elements that, when in contact with tissue, perform a therapeutic or diagnostic function. They can, for example, deliver energy to ablate targeted tissue in the region.

The operative elements often take the form of electrodes carried by a basket assembly surrounding the expandable structure. A push-pull lever causes the electrodes to slide within lumens in the basket arms between a retracted position and an extended position.

The need remains for systems and methods for controlling the actuation and deployment of electrodes from a catheter. In particular, the need remains for actuator systems which can be manufactured in a simple and cost-efficient manner and which are easily manipulated in use.

SUMMARY OF THE INVENTION

The invention provides improved systems and methods for treating a tissue region. On aspect of the invention provides an actuator system for deploying an electrode (or series of electrodes) from a catheter assembly. The actuator system comprises a handle having a trigger lever. The handle carries an actuator rod. The actuator rod is adapted to move the electrode between a retracted position and an extended position. A pinion is carried by a trigger lever for engagement with a rack carried by the actuator rod. The pinion engages the rack upon compression of the trigger lever to move the rack along the actuator rod between a first position corresponding to the electrode being in the retracted position and a second position corresponding to the electrode being in an extended position. In one embodiment, the actuator rod is biased in one of the first and second positions. The actuator rod may be biased in one of the first and second positions by a spring.

According to another aspect of the invention, the system further comprises a locking element for locking the actuator rod in at least one of the first and second positions. In one embodiment, the locking element is spring-loaded. In one embodiment, the locking element is biased in a latched position. The locking element may be biased in the latched position by a spring.

According to another aspect of the invention, at least a portion of the locking element rides along a cam surface as the rack is moved between the first and second positions. In one embodiment, the cam surface is carried by the rack. In another embodiment, the cam surface is carried by the trigger lever.

In one embodiment, the rack includes a detent adapted to receive at least a portion of the locking element in at least one of the first and second positions. In another embodiment, the trigger lever includes a detent adapted to receive at least a portion of the locking element in at least one of the first and second positions.

According to another aspect of the invention, the system provides improved systems and methods for deploying an electrode (or series of electrodes) from a catheter assembly. The actuator assembly comprises a pinion carried by a trigger lever. The actuator assembly also comprises a rack carried by an actuator rod, whereby the pinion engages the rack upon compression of the trigger lever to move the rack along the actuator rod between a first actuator rod position and a second actuator rod position. In one embodiment, the actuator rod is biased in one of the first and second actuator rod positions, and may be biased by a spring.

According to yet another aspect of the invention, the assembly further comprises an electrode advancer mandrel operating in a biased relationship to the actuator rod and a locking element for locking the electrode advancer mandrel in at least one of a first and second electrode advancer mandrel position. In one embodiment, the electrode advancer mandrel includes a sear for cooperating with the locking element and a sear release for releasing the sear and allowing the electrode advancer mandrel to advance to an electrode extended position. The assembly may also include a retraction member for moving the actuator rod from the second actuator position back to the first actuator rod position.

Other features and advantages of the inventions are set forth in the following Description and drawings, as well as in the appended claims.

BRIEF DESCRIPTION OF THE DRAWINGS

FIG. 13 is a view similar to FIG. 12 illustrating the rack in a second position and the locking mechanism latched.

FIG. 13A is a detailed view of the locking mechanism as shown in FIG. 13.

FIG. 14 is a view similar to FIG. 13 illustrating the release of the locking mechanism.

FIG. 14A is a detailed view of the locking mechanism as shown in FIG. 13.

FIG. 17 is a view similar to FIG. 16 illustrating the rack in a second position and the spring-loaded firing mechanism in the firing position.

FIG. 18 is a view similar to FIG. 17 illustrating the release of the locking mechanism.

FIG. 19 is a view similar to FIG. 16 illustrating the retraction process with the rack returned to the first position and the locking mechanism returned to the locked position.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

This Specification discloses various catheter-based systems and methods for treating dysfunction in various locations in an animal body. For example, the various aspects of the invention have application in procedures requiring treatment of sphincters and adjoining tissue regions in the body, or hemorrhoids, or incontinence, or obesity, or restoring compliance to or otherwise tightening interior tissue or muscle regions. The systems and methods that embody features of the invention are also adaptable for use with systems and surgical techniques that are not necessarily catheter-based.

The systems and methods are particularly well suited for treating dysfunctions in the upper gastrointestinal tract, e.g., in the lower esophageal sphincter and adjacent cardia of the stomach. For this reason, the systems and methods will be described in this context. Still, it should be appreciated that the disclosed systems and methods are applicable for use in treating other dysfunctions elsewhere in the body, which are not necessarily sphincter-related.

I. Overview

Figure 1:
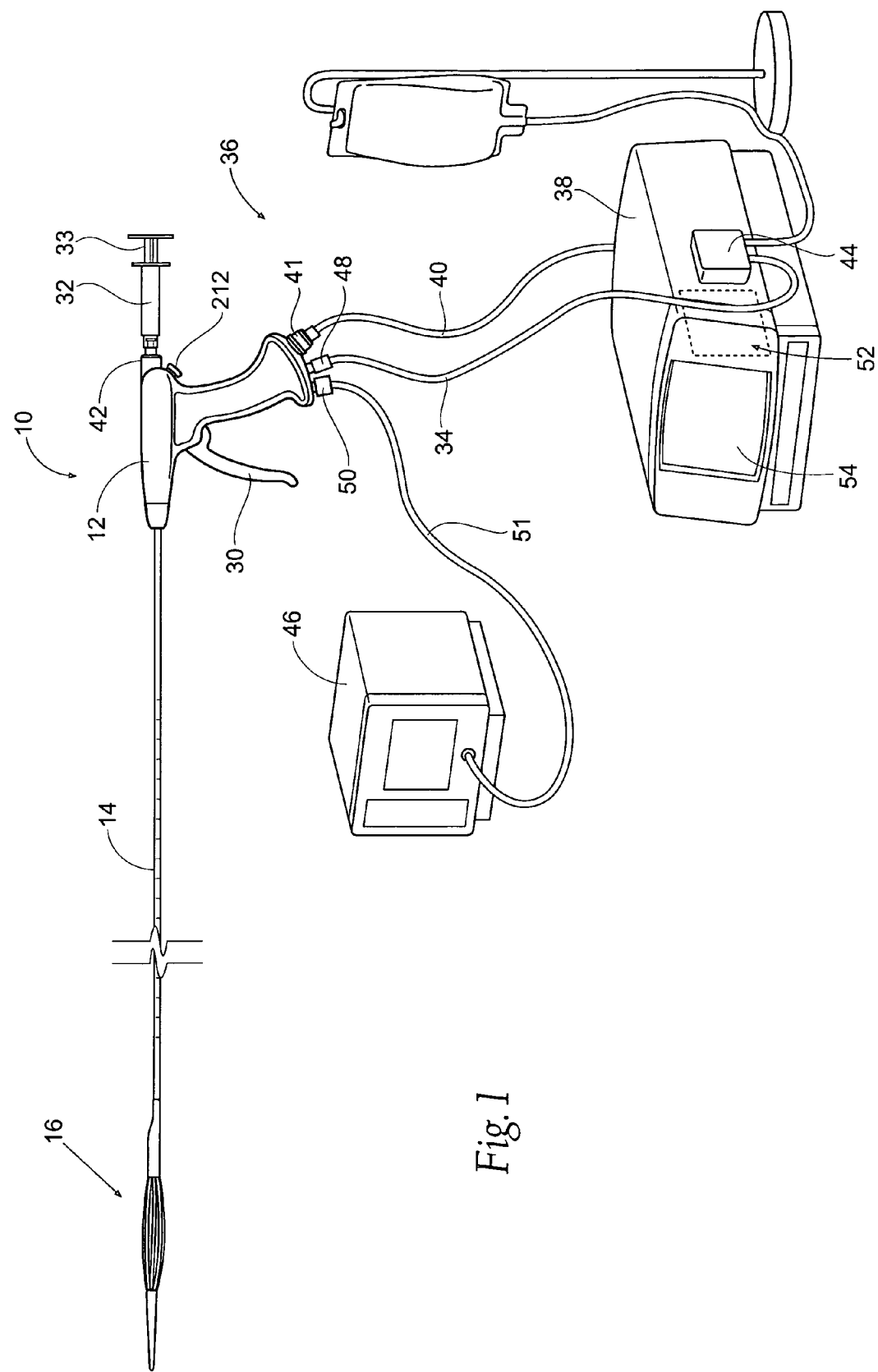
FIG. 1 is a schematic view of a system for treating tissue.

A tissue treatment device 10 and associated system 36 are shown in FIG. 1.

The device 10 includes a handle 12 made, e.g., from molded plastic. The handle 12 carries a flexible catheter tube 14 constructed, for example, by extrusion using standard flexible, medical grade plastic materials, like Pebax™ plastic material, vinyl, nylon, poly(ethylene), ionomer, poly(urethane), poly(amide), and poly(ethylene terephthalate). The handle 12 is sized to be conveniently held by a physician, to introduce the catheter tube 14 into the tissue region targeted for treatment. The catheter tube 14 may be deployed with or without the use of a guide wire.

The catheter tube 14 carries on its distal end an operative element 16. The operative element 16 can take different forms and can be used for either therapeutic purposes, or diagnostic purposes, or both. The operative element 16 can support, for example, a device for imaging body tissue, such as an endoscope, or an ultrasound transducer. The operative element 16 can also support a device to deliver a drug or therapeutic material to body tissue. The operative element 16 can also support a device for sensing a physiological characteristic in tissue, such as electrical activity, or for transmitting energy to stimulate tissue or to form lesions in tissue.

Figure 2:
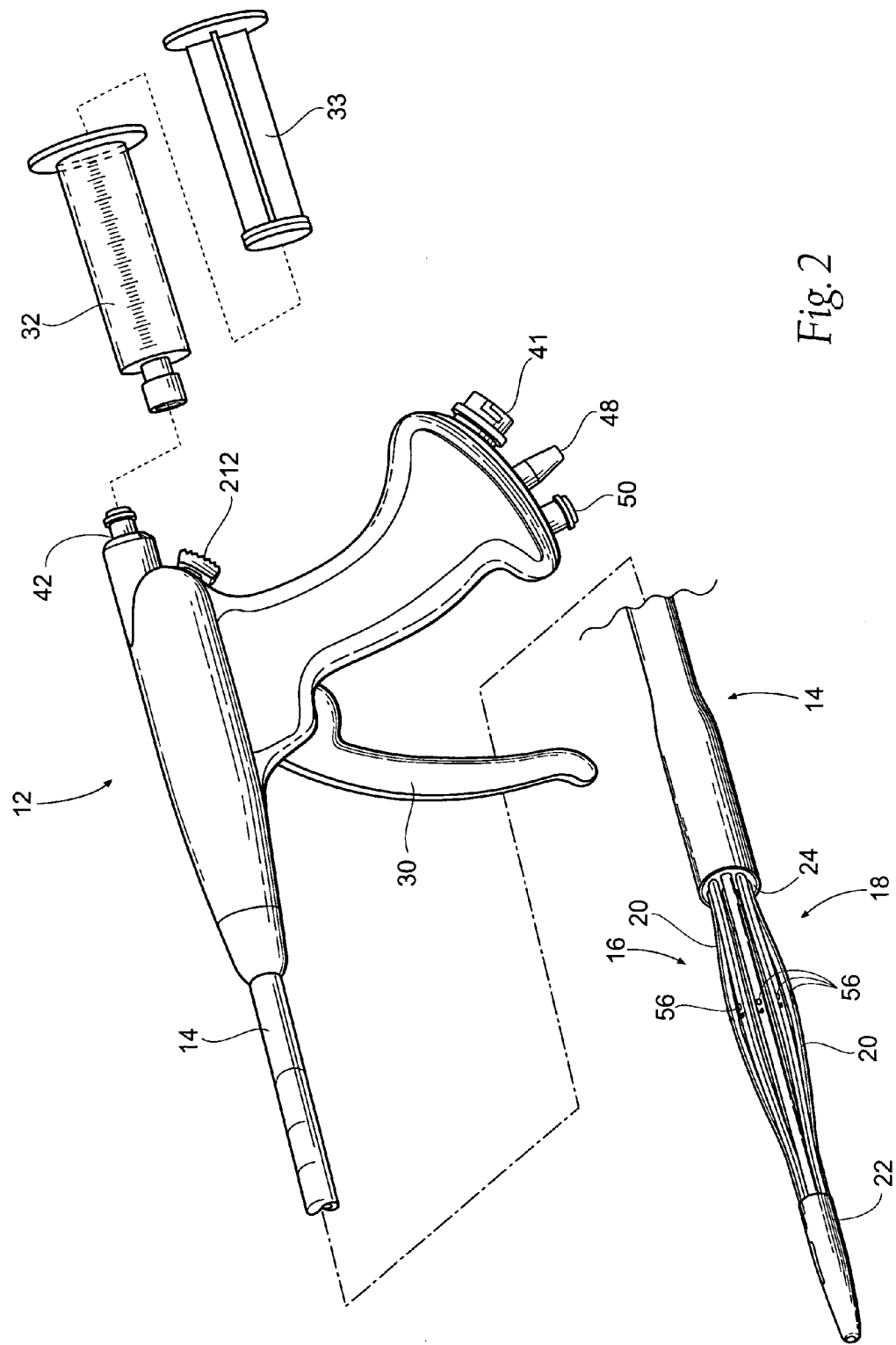
FIG. 2 is an enlarged view of the treatment device, with parts broken away and in section, that is associated with the system shown in FIG. 1, the treatment device comprising basket structure that carries selectively deployable electrode elements and that expands in response to inflation of an interior balloon structure, FIG. 2 showing the basket in a collapsed condition with the electrode elements retracted.
Figure 3:
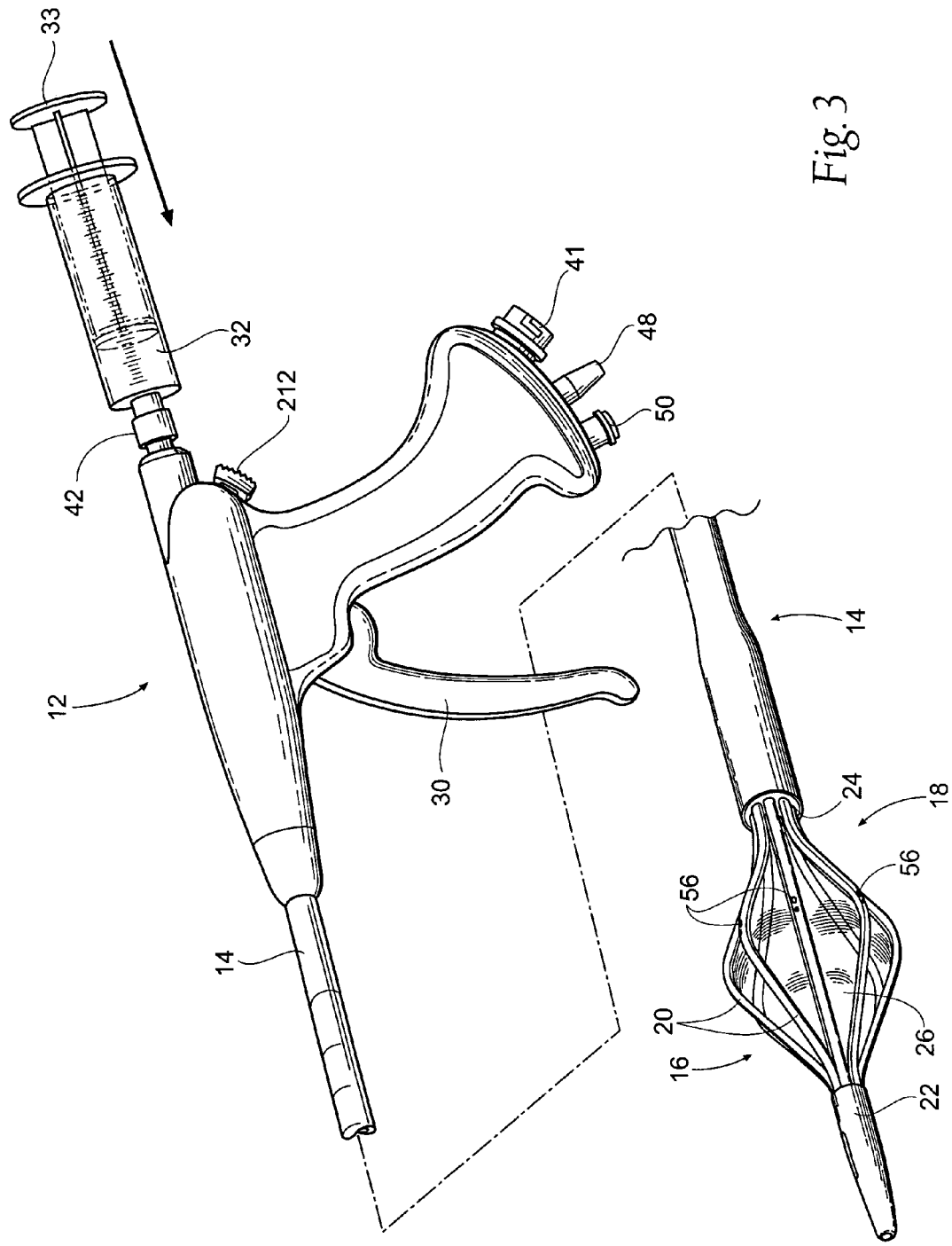
FIG. 3 is an enlarged view of the treatment device shown in FIG. 2, with the basket expanded due to inflation of interior balloon structure and the electrode elements still retracted.
Figure 4:
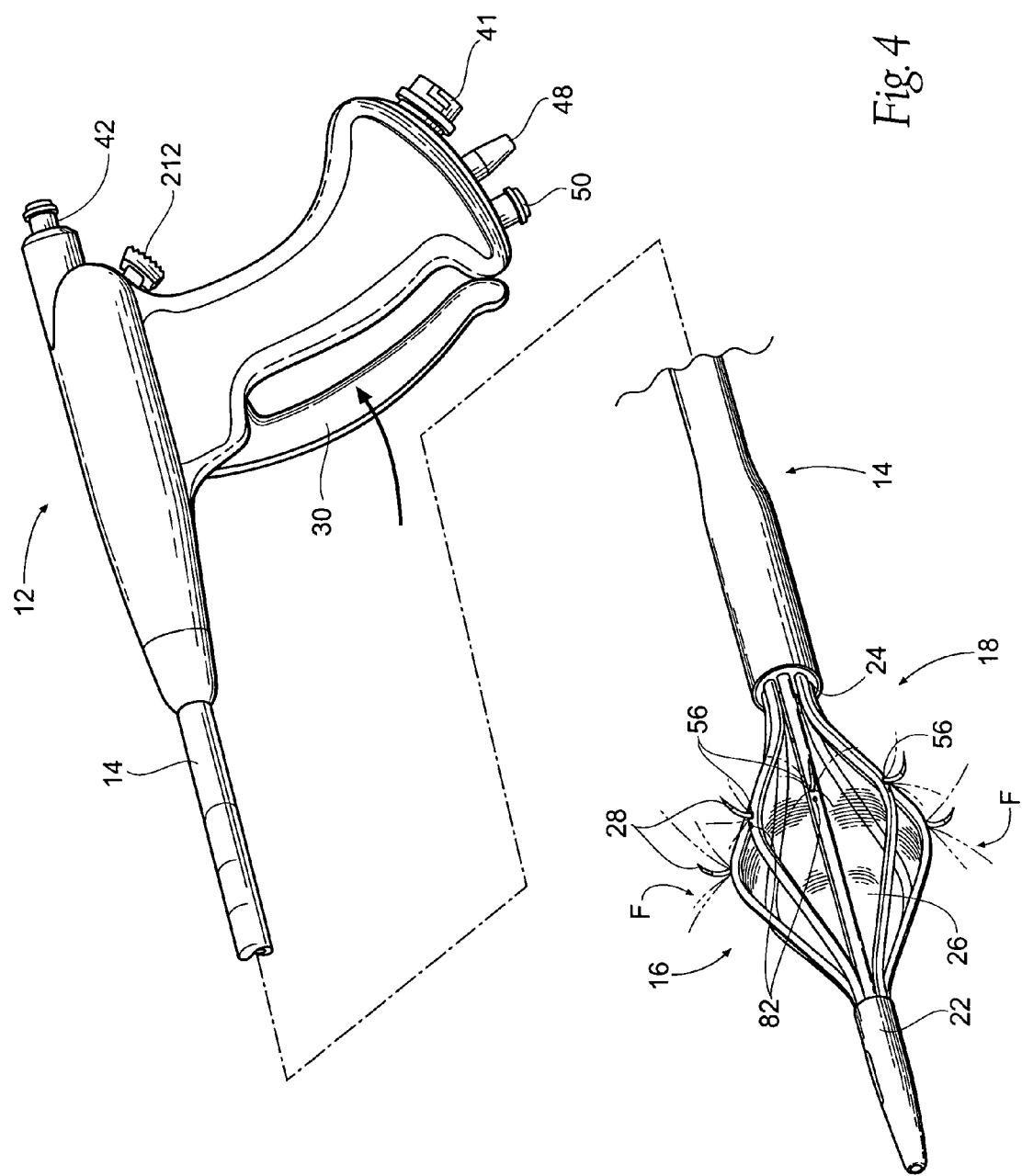
FIG. 4 is an enlarged view of the treatment device shown in FIG. 2, with the basket expanded due to inflation of interior balloon structure and the electrode elements extended for use, FIG. 4 also showing the passage of irrigation fluid from the basket to cool the surface tissue while radio-frequency energy is applied by the electrode elements to subsurface tissue.

In the embodiment shown in FIGS. 2 to 4, the operative element 16 comprises a three-dimensional basket 18. The basket 18 includes an array of arms 20. The arms 20 are desirably made from extruded or molded plastic, but they could also be formed from stainless steel or nickel titanium alloy. As shown in FIG. 2, the arms 20 are assembled together between a distal tip 22 and a proximal base element 24.

As FIGS. 3 and 4 show, an expandable structure 26 comprising, e.g., a balloon, is located within the basket 18. The expandable balloon structure 26 can be made, e.g., from a Polyethylene Terephthalate (PET) material, or a polyamide (non-compliant) material, or a radiation cross-linked polyethylene (semi-compliant) material, or a latex material, or a silicone material, or a C-Flex (highly compliant) material. Non-compliant materials offer the advantages of a predictable size and pressure feedback when inflated in contact with tissue. Compliant materials offer the advantages of variable sizes and shape conformance to adjacent tissue geometries.

The balloon structure 26 presents a normally, generally collapsed condition, as FIG. 2 shows. In this condition, the basket 18 is also normally collapsed about the balloon structure 26, presenting a low profile for deployment into the targeted tissue region.

Expansion of the balloon structure 26, e.g., by the introduction of air through a syringe 32 and plunger 33 coupled to a one-way check valve fitting 42 on the handle 12 (see FIG. 3), urges the arms 20 of the basket 18 to open and expand, as FIG. 3 shows. The force exerted by the balloon structure 26 upon the basket arms 20, when expanded, is sufficient to exert an opening force upon the tissue surrounding the basket 18.

Figure 5:
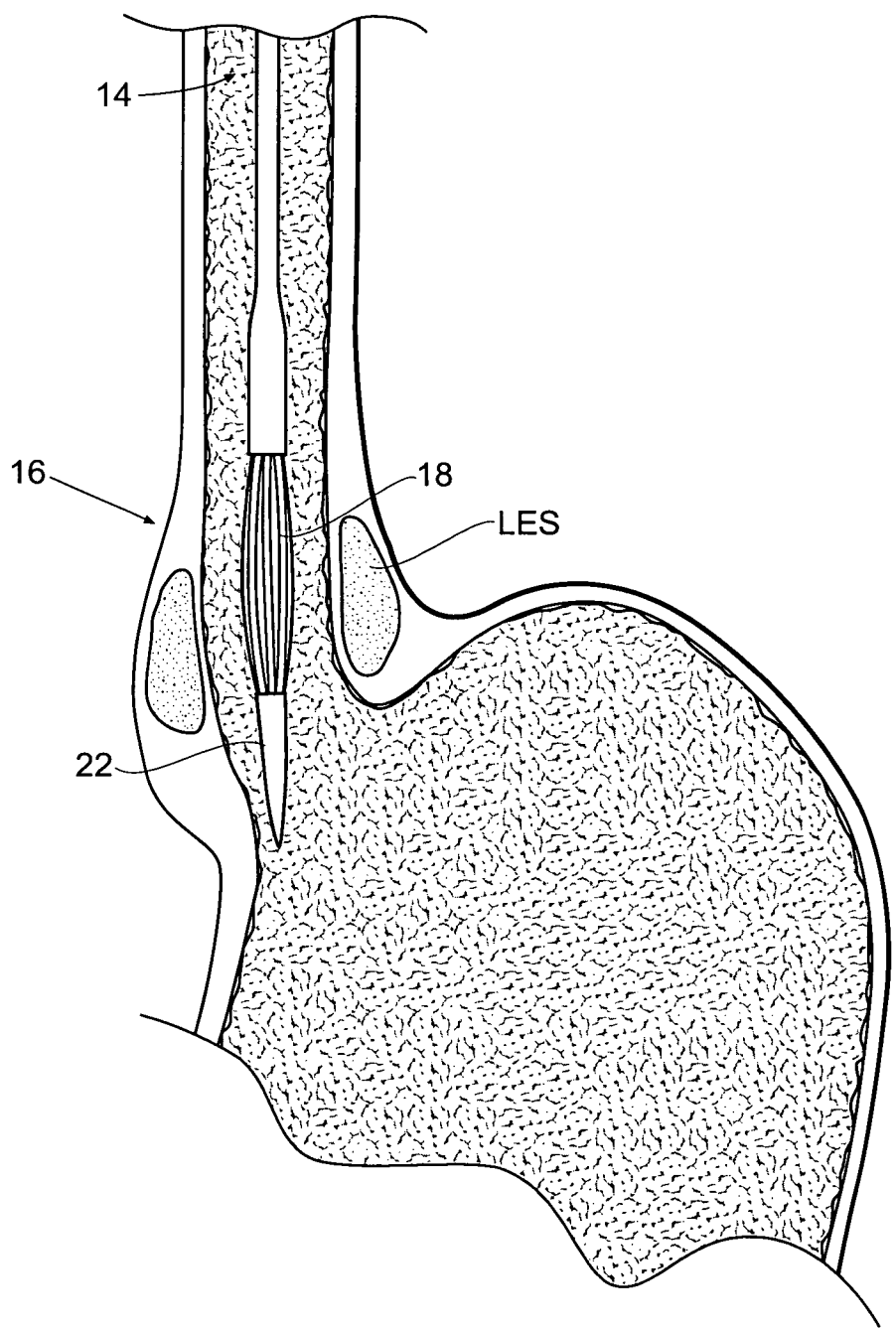
FIGS. 5 to 7 are simplified anatomic views showing the use of the treatment device shown in FIGS. 2 to 4 deployed in the region of the lower esophageal sphincter to form an array of lesions.
Figure 6:
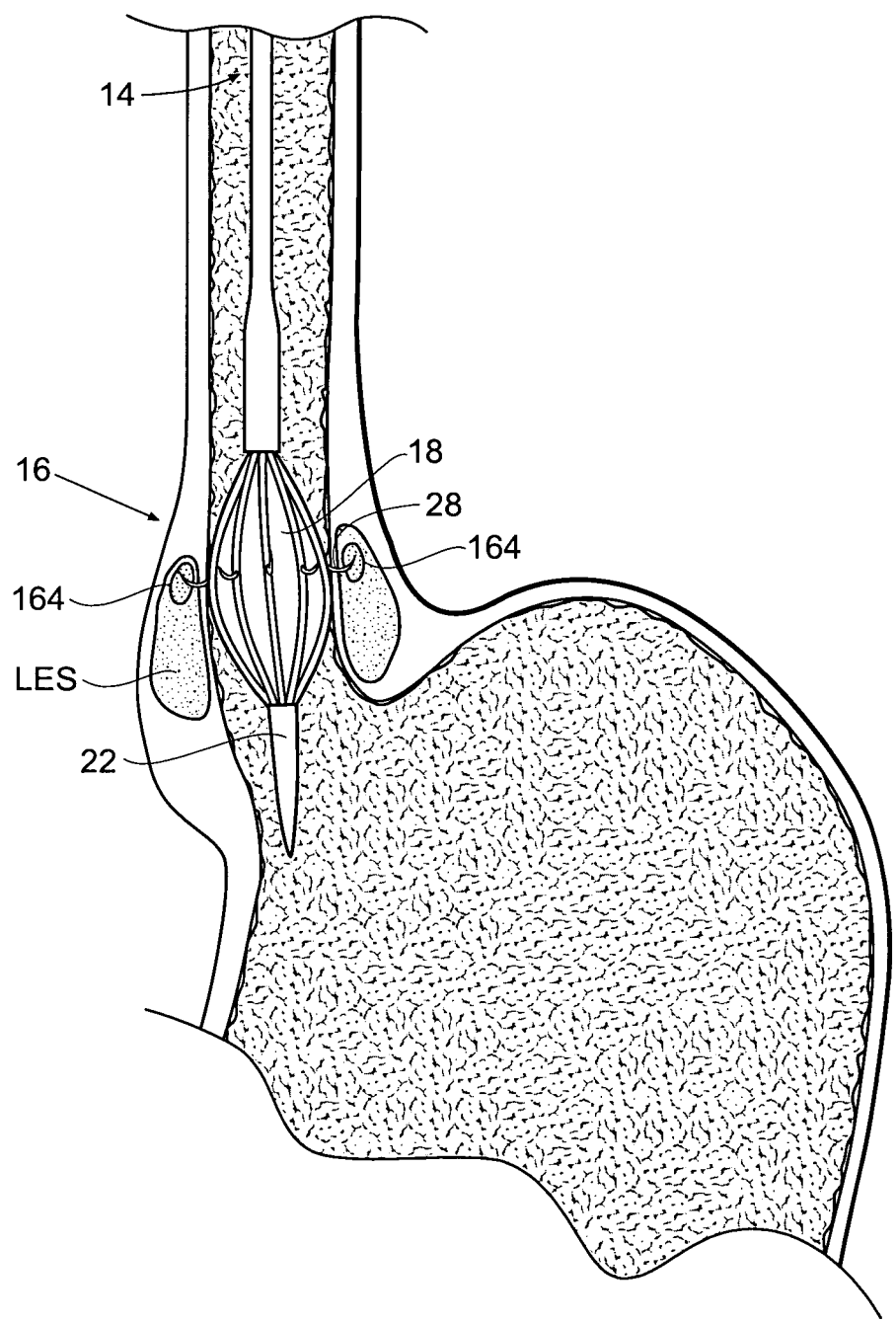

For the purpose of illustration (see FIGS. 5 and 6), the targeted tissue region comprises the lower esophageal sphincter (LES) and cardia of the stomach. When deployed in this or any sphincter region, the opening force exerted by the balloon structure 26 serves to dilate the sphincter region, as FIG. 6 shows.

Each basket arm 20 carries an electrode element 28. A trigger-type lever 30 on the handle (see FIG. 4) is mechanically coupled through the catheter tube 14 to the electrode elements 28, as will be described in detail later. In use, squeezing pressure on the lever 30 causes the electrode elements 28 to slide within the lumens in the basket arms 20 between a retracted position (shown in the FIG. 3) and an extended position (shown in FIG. 4). As FIG. 4 shows, the electrode element 28, when extended, projects through an opening 56 in the basket arm. When deployed in the tissue region (see FIG. 6), the extended electrode element 28 pierces tissue. As FIG. 4 shows, temperature sensing elements 82 (e.g., thermocouples) are desirably carried by the arms 20 near the electrode elements 28 to sense tissue temperature conditions.

In a desired arrangement, the electrode elements 28 deliver radio frequency energy, e.g., energy having a frequency in the range of about 400 kHz to about 10 mHz. A return path is established, e.g., by an external patch electrode, also called an indifferent electrode. In this arrangement, the application of radio frequency energy serves to ohmically heat tissue in the vicinity of the electrode elements 28, to thermally injure the tissue and form the localized sub-surface lesions 164, which are shown in FIG. 6. Of course, tissue heating can be accomplished by other means, e.g., by coherent or incoherent light; heated or cooled fluid; resistive heating; microwave; ultrasound; a tissue heating fluid; or cryogenic fluid.

In this arrangement, the natural healing of subsurface lesions or pattern of subsurface lesions created by the applied energy leads to a physical tightening of the sphincter and/or adjoining cardia and/or a reduction in the compliance of these tissues. The subsurface lesions can also result in the interruption of aberrant electrical pathways that may cause spontaneous sphincter relaxation. In any event, the treatment can restore normal closure function to the sphincter.

The electrode elements 28 can be formed from various energy transmitting materials. For deployment in the esophagus or cardia of the stomach, the electrode elements 28 are formed, e.g., from nickel titanium. The electrode elements 28 can also be formed from stainless steel, e.g., 304 stainless steel, or a combination of nickel titanium and stainless steel.

In this arrangement, the electrode element 28 may comprise a hybrid of materials comprising stainless steel for the proximal portion and nickel titanium alloy for the distal portion.

The exterior surface of each electrode element 28 can carry an electrical insulating material, except at its distal region, where the radio frequency energy is applied to tissue. The presence of the insulating material serves to preserve and protect the mucosal tissue surface from exposure to the radio frequency energy, and, thus, from thermal damage. The insulating material can comprise, e.g., a Polyethylene Terephthalate (PET) material, or a polyimide or polyamide material.

As FIG. 1 shows, the treatment device 10 desirably operates as part of a system 36. The system 36 includes a generator 38 to supply the treatment energy to the operative element 16. In the illustrated embodiment, the generator 38 supplies radio frequency energy to the electrodes 28. A cable 40 plugged into a connector 41 on the handle 12 electrically couples the electrode elements 28 to the generator 38. Electrode supply wires pass through the catheter tube 14 from the handle to the electrode elements 28.

The system 36 can also include certain auxiliary processing equipment. In the illustrated embodiment, the processing equipment comprises an external fluid delivery or irrigation apparatus 44. In the illustrated embodiment, the fluid delivery apparatus 44 comprises an integrated, self priming peristaltic pump rotor that is carried on a side panel of the generator 38. Other types of non-invasive pumping mechanisms can be used, e.g., a syringe pump, a shuttle pump, or a diaphragm pump.

A luer fitting 48 on the handle 12 couples to tubing 34 to connect the treatment device 10 to the fluid delivery apparatus 44. Irrigation supply tubing in the catheter tube 14 conveys irrigation fluid through a lumen in each basket arm 20 for discharge through irrigation openings 56 (see FIG. 4) by or near the electrode elements 28. This provides localized cooling of surface tissue. In the illustrated embodiment, the irrigation fluid (designated F in FIG. 4) is discharged directly at the base of each electrode element 28. In this arrangement, the irrigation fluid is conveyed through the same basket arm lumen and is discharged through the same basket arm opening 56 as the electrode element 28. Of course, other irrigation paths can be used.

In this arrangement, the processing equipment desirably includes an aspiration source 46. Another luer fitting 50 on the handle 12 couples tubing 51 to connect the treatment device 10 to the aspiration source 46. The aspiration source 46 draws irrigation fluid discharged by or near the electrodes 28 away from the tissue region. The aspiration source 46 can comprise, for example, a vacuum source, which is typically present in a physician's suite.

The system 36 also desirably includes a controller 52. The controller 52 is linked to the generator 38 and the fluid delivery apparatus 44. The controller 52, which preferably includes an onboard central processing unit, governs the power levels, cycles, and duration that the radio frequency energy is distributed to the electrodes 28, to achieve and maintain temperature levels appropriate to achieve the desired treatment objectives. In tandem, the controller 52 also desirably governs the delivery of irrigation fluid.

The controller 52 desirably includes an input/output (I/O) device 54. The I/O device 54, which can employ a graphical user interface, allows the physician to input control and processing variables, to enable the controller to generate appropriate command signals.

Figure 7:
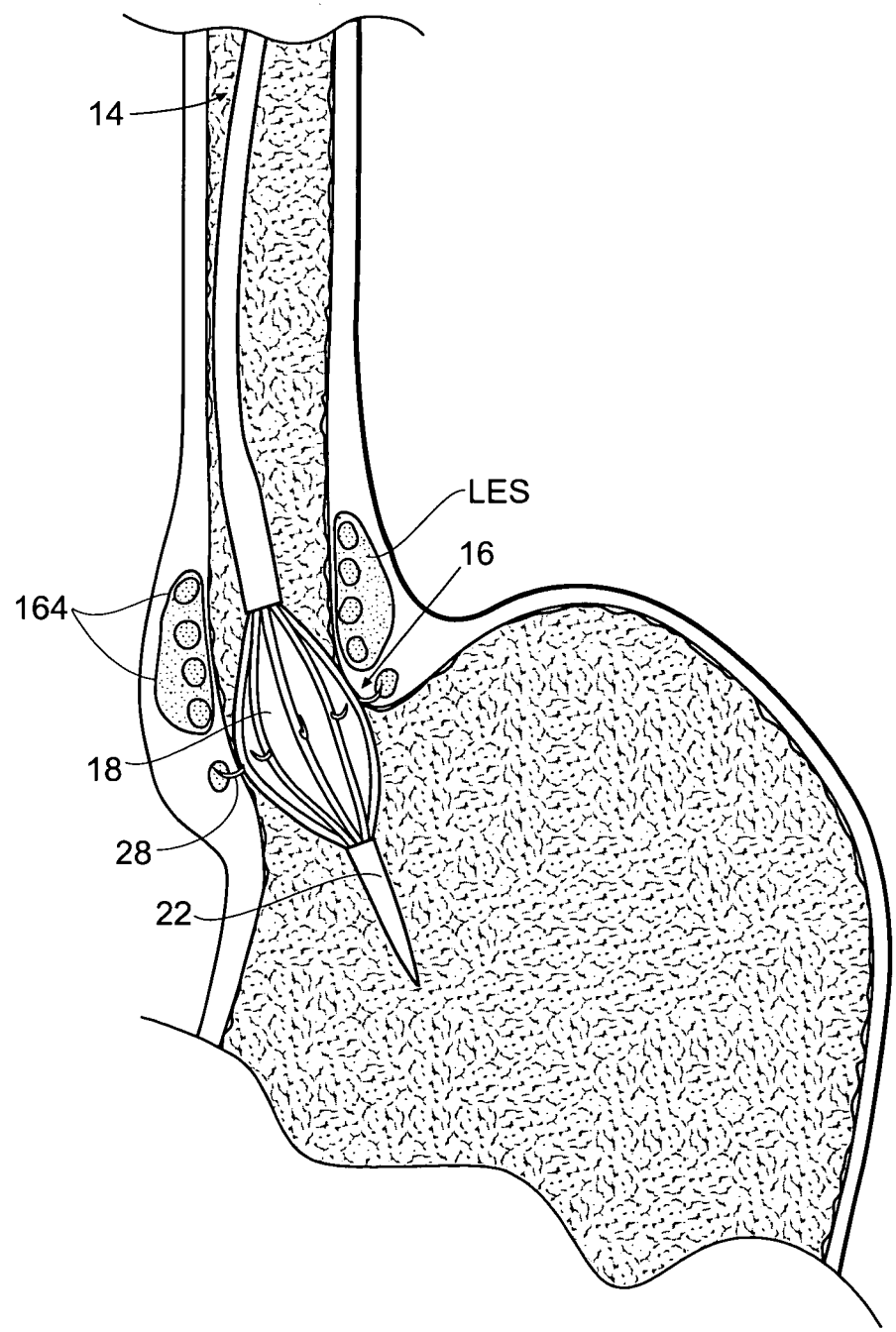

In use (see FIGS. 5 to 7), the operative element 16 can be deployed at or near the lower esophageal sphincter (LES) for the purpose of treating GERD. A physician can use the visualization functions of, e.g., an endoscope to obtain proper position and alignment of the operative element 16 with the LES.

Once proper position and alignment are achieved (see FIG. 6), the physician can expand the balloon structure 16 and extend the electrode elements 16 into piercing contact with tissue at or near the LES. Application of ablation energy forms the lesions 164. Retraction of the electrode elements 28 and collapsing of the balloon structure 16 allows the physician to reposition the operative element 16 and perform one or more additional ablation sequences (see FIG. 7). In this way, the physician forms a desired pattern of circumferentially and axially spaced lesions 164 at or near the LES and cardia.

II. Handle

Figure 8:
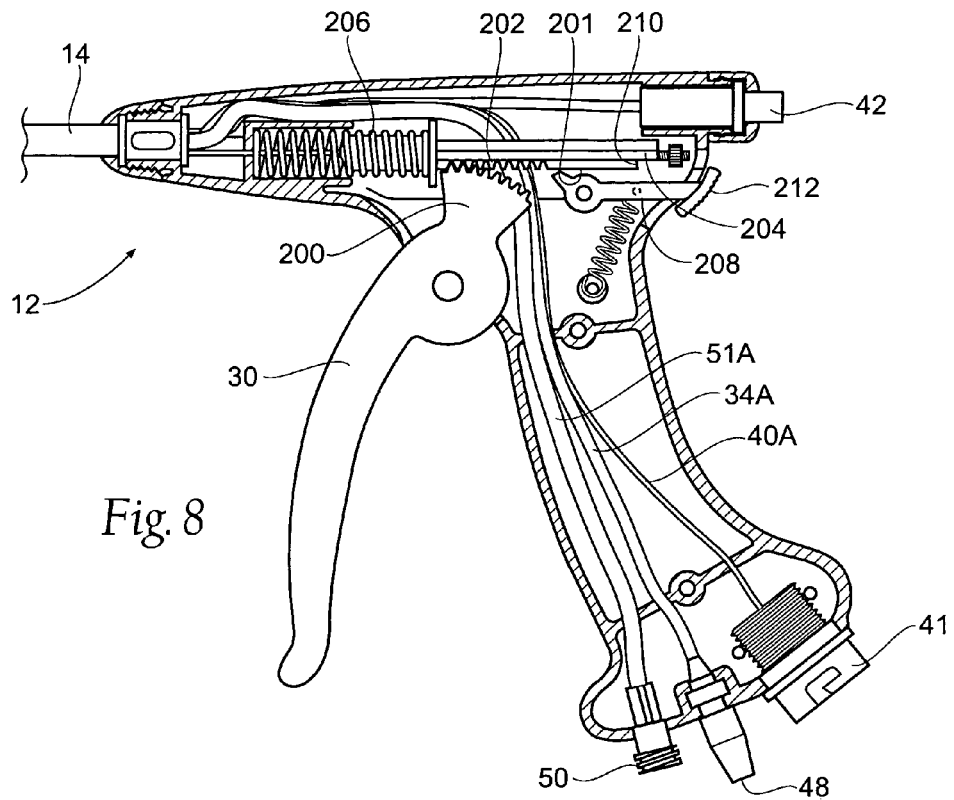
FIG. 8 is a side sectional view of the catheter handle illustrating a rack and pinion trigger mechanism for moving treatment electrodes between a retracted position and an extended position and illustrating the rack in a first position and the locking mechanism unlatched.
Figure 9:
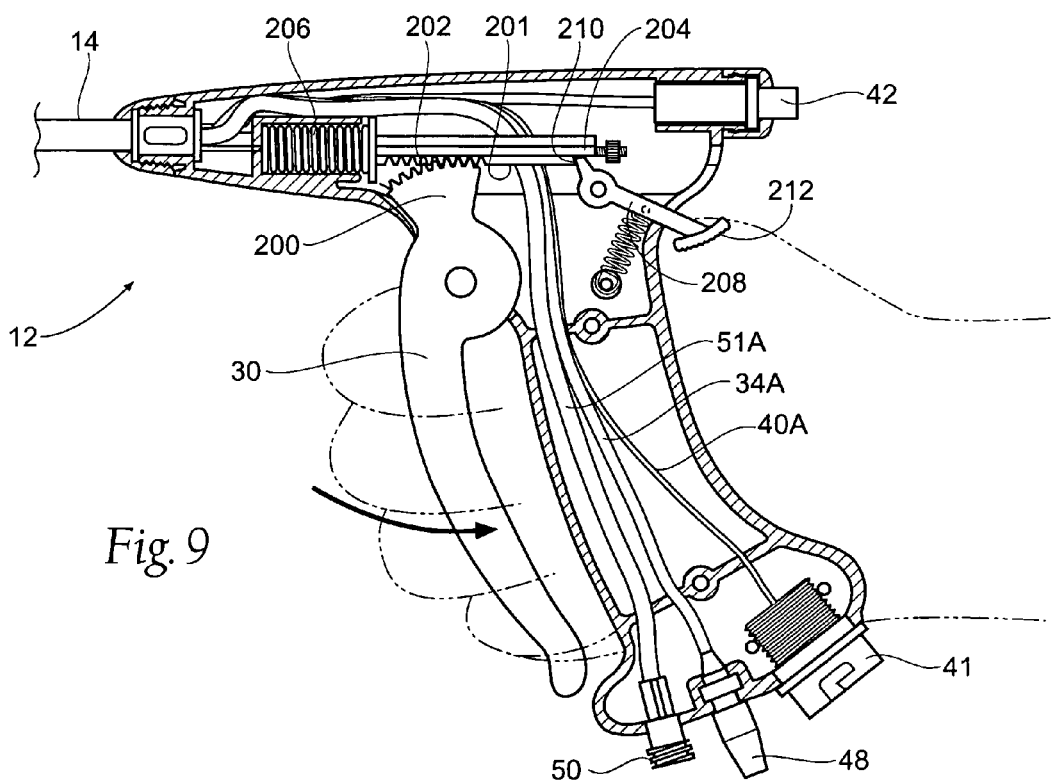
FIG. 9 is a view similar to FIG. 8 illustrating the rack in a second position and the locking mechanism latched.
Figure 10:
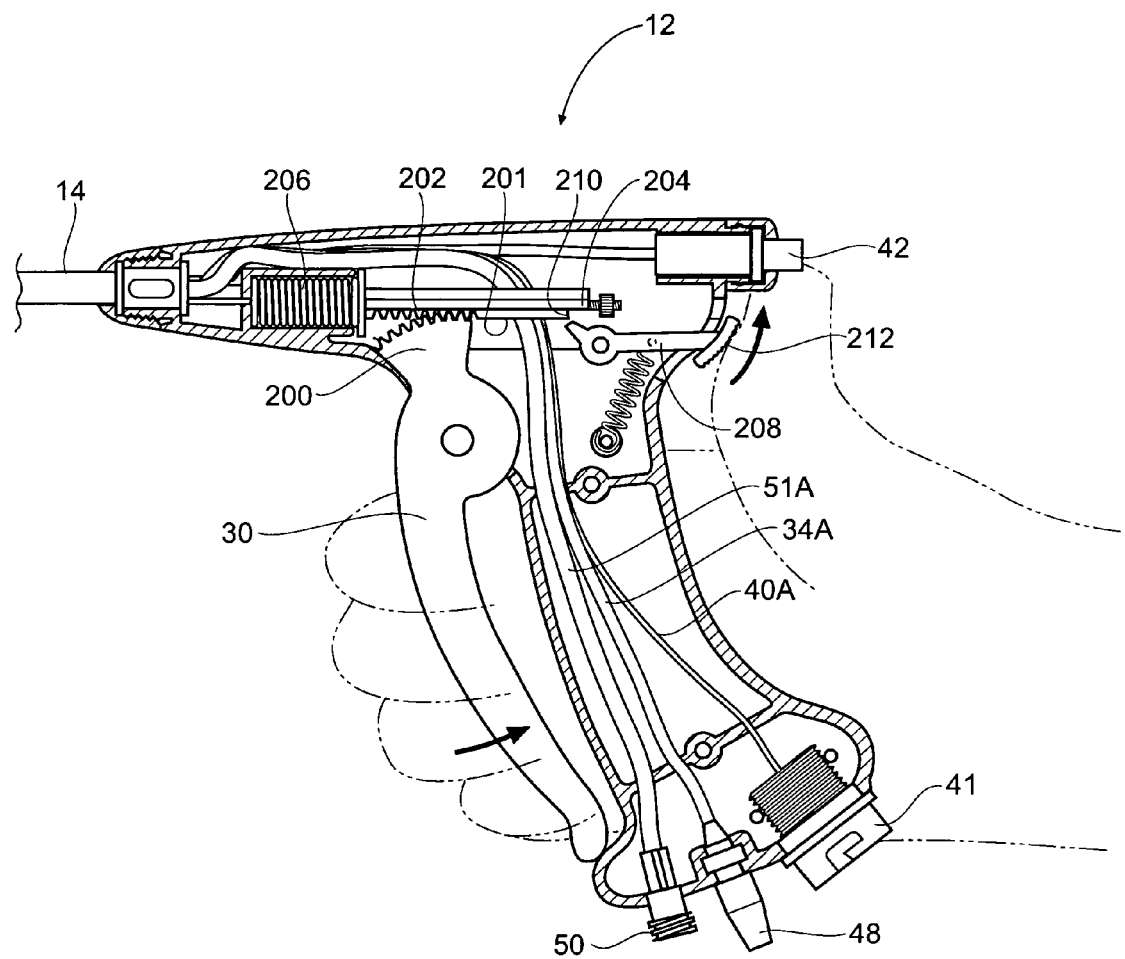
FIG. 10 is a view similar to FIG. 8 illustrating the release of the locking mechanism.
Figure 11:
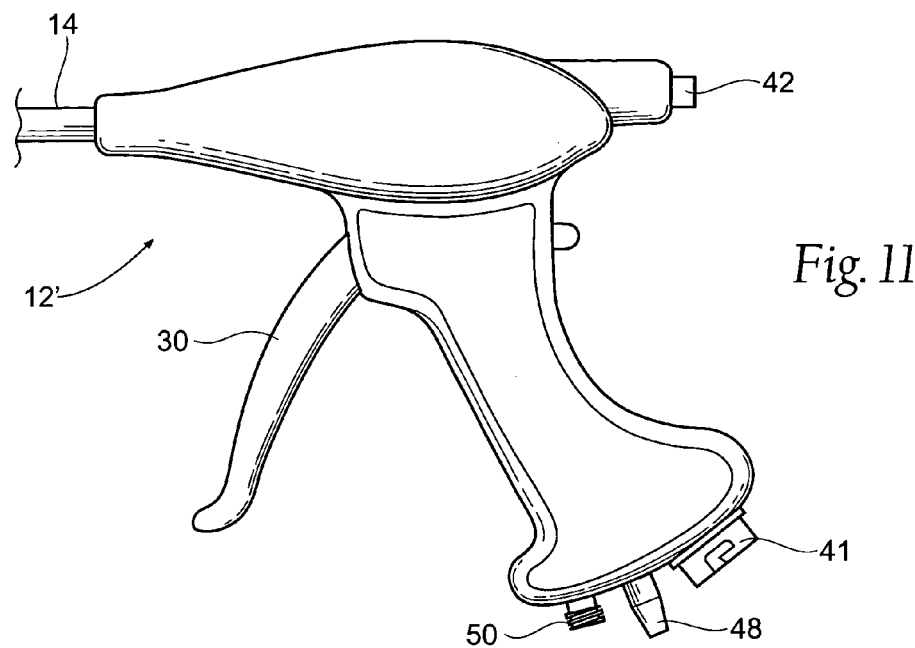
FIG. 11 is a perspective view of an alternative embodiment of a catheter handle having a rack and pinion trigger mechanism.
Figure 12:
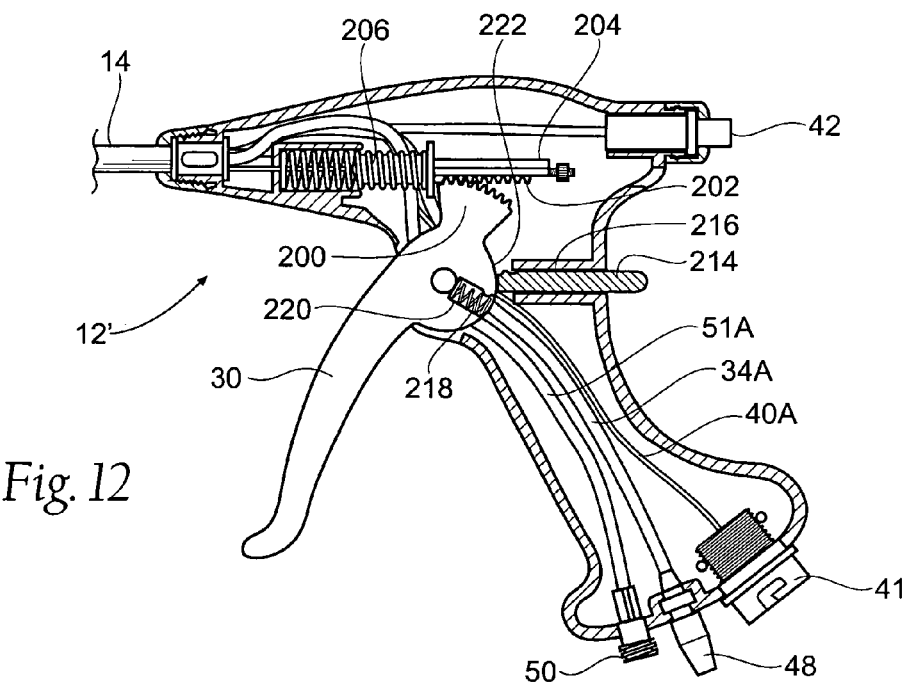
FIG. 12 is a side sectional view of the handle shown in FIG. 11 and illustrating the rack in a first position and the locking mechanism unlatched.
Figure 15:
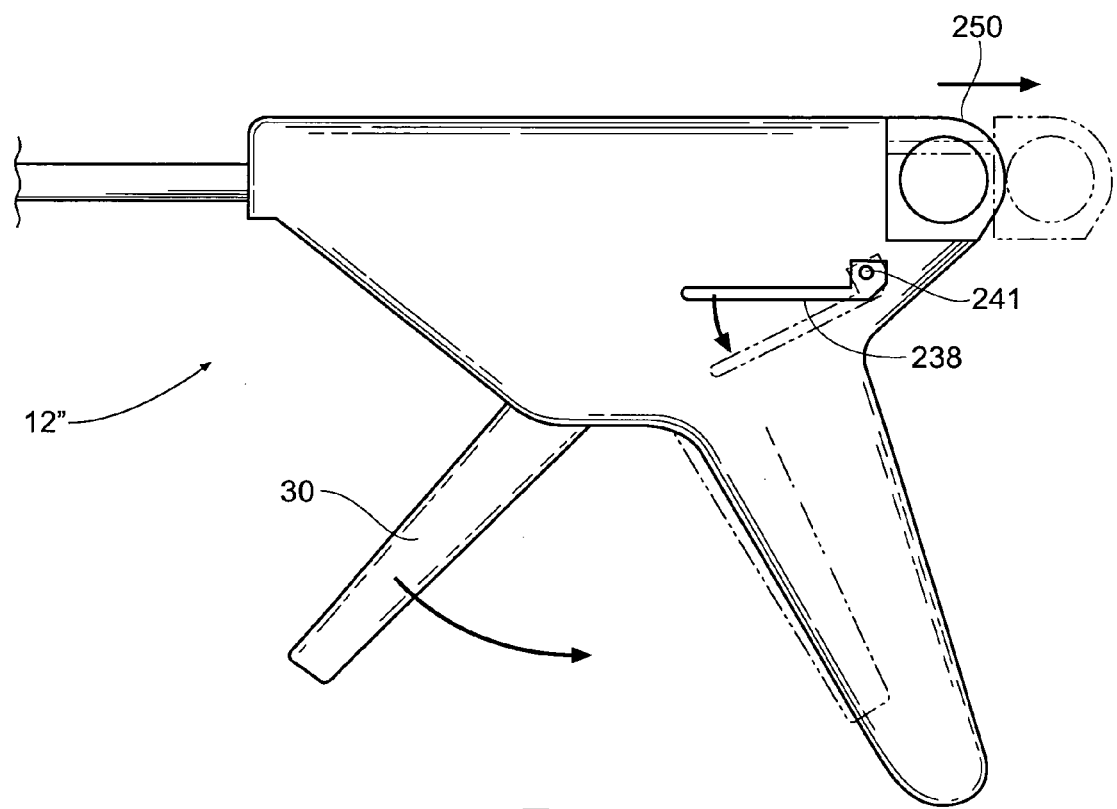
FIG. 15 is a perspective view of an alternative embodiment of a catheter handle having a rack and pinion trigger mechanism, a spring-loaded firing mechanism, and a retraction pull bar.

The handle 12 can provide any of a variety of different mechanisms to selectively control the advancement and retraction of the electrodes 28. FIGS. 8 to 10 further illustrate the handle 12, which employs a trigger-type mechanism. While the trigger-type mechanism will be described in relation to actuating and controlling advancement and retraction of electrodes 28, it is to be understood that the mechanism is also suitable for use in the deployment or actuation of a variety of other medical and non-medical devices.

The handle 12 permits passage of aspiration tubing 51A, irrigation tubing 34A, and electrical conduit 40A from the catheter 14 through the handle 12 to permit coupling of tubing 51A, tubing 34A, and conduit 40A to aspiration leur fitting 50, fluid source leur fitting 48, and electrical cable connector 41 respectively.

In the illustrated embodiment, the handle 12 includes a "rack and pinion" type control mechanism. A pinion 200 is carried by the trigger lever or arm 30. A complementary rack 202 is carried by an actuator rod 204. The pinion 200 controls fore and aft movement of the rack 202 along the rod 204 between a first (retracted) position (shown in FIG. 8) and a second (extended) position (shown in FIG. 9).

Compression of the arm 30 (e.g., by squeezing) causes the pinion 200 to engage the rack 202 and advance the rack 202 along the rod 204. Advancement of the rack 202 moves the electrodes 28 from the retracted position (shown in FIG. 3) to the extended position (shown in FIG. 4). Release of pressure on the arm 30 causes the rack 202 to be moved in the reverse direction to move the electrodes 28 from the extended to the retracted position.

A control element can be provided to bias the rack 202 in either the first or second position. In the illustrated embodiment, the control element takes the form of an actuator spring 206. The spring 206 is compressed by movement of the rod 204 in a first direction and relaxes upon movement of the rod 204 in the reverse direction.

In a preferred embodiment, the spring 206 is normally biased in the relaxed position (shown in FIG. 8), in which the rack 202 is in the first position and the electrodes 28 are retracted. Advancement of the rack 202 compresses the spring 206 to overcome the bias and advance the rod 204 to the second position to extend the electrodes 28.

A locking mechanism is desirably provided to secure the rack and pinion mechanism in a desired position. In the illustrated embodiment, the locking mechanism takes the form of a spring-loaded pawl lock 208. The pawl lock 208 travels along a cam surface 201 on the rack 202 and falls into a detent 210 at the proximal end of the rack 202 to latch and secure the rack 202 in the second position (in which the electrodes 28 are extended).

The lock 208 is normally biased in this latched position (shown in FIG. 9). Slight compression of the arm 30 releases the tension of the lock 208 within the detent 210 to permit manipulation of a tab 212 (e.g., upward pressure on the tab 212 by a thumb or finger) to release the lock 208 from the detent 210 (shown in FIG. 10) and automatically returns the rack 202 to the first position (in which the electrodes 28 are retracted). In the illustrated embodiment, the tab 212 is desirably positioned to permit single-handed compression of the trigger arm 30 and manipulation of the lock 208, allowing the other hand of the physician to remain free.

In use, with the electrodes 28 in the retracted position, the physician advances the treatment device 10 to the targeted tissue region. The physician gently squeezes the trigger arm 30 to advance the rack 202 to the second position and extend the electrodes 28. The physician maintains squeezing pressure on the arm 30 until the lock 208 is secured in the latched position. The desired treatment is then administered. The physician then applies gentle pressure to the arm 30 while simultaneously applying upward pressure to the locking tab 212 to release the lock 208. This returns the rack 202 to the first position and retracts the electrodes 28. The treatment device 10 can then be repositioned to administer additional treatment or the device 10 can be withdrawn.

FIGS. 11 to 14A illustrate an alternative embodiment of a handle 12' employing a trigger-type mechanism. The handle 12' shares many features of the first embodiment of the handle 12 just described. Like structural elements are therefore assigned like reference numbers.

Like the handle 12 previously described, the handle 12' employs a rack and pinion mechanism to control extension and retraction of the electrodes 28. Also like the embodiment previously described, advancement of the rack 202 compresses the actuator spring 206 to overcome the bias and advance the rod 204 from the first position to the second position and extend the electrodes 28.

Also similar to the embodiment previously described, the handle 12' provides a spring-loaded locking mechanism. In the illustrated embodiment, a locking pin 214 is carried within a bore or recess 216 within the handle housing. The trigger arm 30 desirably provides a spring 218 within a detent 220 for engaging the pin 214. The spring-loaded locking mechanism may also include a latching mechanism to assist in maintaining the position of the locking pin 214 (see FIGS. 13A and 14A). Desirably, the locking pin 214 may include a detent or groove 215 positioned near the trigger arm engaging end, and the detent 220 within the trigger arm 30 may include a mating latch 221. It is to be appreciated other latching mechanism configurations may be used, such as the detent 220 may include the detent or groove and the locking pin 214 may include the mating latch.

In use, with the electrodes 28 in the retracted position, the physician advances the treatment device 10 to the targeted tissue region. As can be seen in FIG. 13, the physician then compresses the trigger 30 while simultaneously applying slight pressure on the pin 214. The pin 214 is desirably positioned to permit single-handed compression of the trigger arm 30 and manipulation of the pin 214. The pin 214 travels along an arcuate cam surface 222 of the arm 30 as the pinion 200 moves along the rack 202 and then falls into the detent 220 on the arm 30 to latch and secure the rack 202 in the second position (in which the electrodes 28 are extended).

The latching means allows the lock to be normally biased in this latched position (shown in FIGS. 13 and 13A). Slight compression of the arm 30 to an intermediate position (see FIG. 14) allows the compressive force on the spring 218 to overcome the latching mechanism's hold on the pin 214, and thus allows the release of the pin 214 from the detent 220 (shown in FIGS. 14 and 14A). The physician then releases the trigger allowing the rack 202 to automatically return to the first position (shown in FIG. 12) to retract the electrodes 28.

FIGS. 15 to 19 illustrate an additional alternative embodiment of a handle 12" employing a trigger-type mechanism, a spring-loaded firing mechanism, and a retraction pull bar. The handle 12" shares many features of the embodiments of the handle 12 and 12' just described. Like structural elements are therefore assigned like reference numbers. While the handle 12" will be described in relation to actuating and controlling advancement and retraction of electrodes 28, it is to be understood that the handle and mechanisms are also suitable for use in the deployment or actuation of a variety of other medical and non-medical devices.

The handle 12" may also permit passage of additional operative elements such as those shown in FIGS. 8 to 14. The operative elements may include, but are not limited to, aspiration tubing, irrigation tubing, and electrical conduit from the catheter 14 through the handle 12" for incorporation with the system 36.

Like the handles 12 and 12' previously described, the handle 12" employs a rack and pinion mechanism. In this embodiment, the rack and pinion mechanism serves to prime the spring-loaded firing mechanism. A pinion 200 is carried by the trigger lever or arm 30. A complementary rack 202 is carried by an actuator rod 204. The pinion 200 controls fore and aft movement of the rack 202 along the rod 204 between a first (electrode retracted) position (shown in FIG. 16) and a second (primed firing mechanism) position (shown in FIG. 17). A trigger or sear latch 238, which may pivot on a pin 241, is now ready to be moved or rotated from a first position to a second position in order to fire the electrodes 28 from a retracted position to an extended position.

In this illustrated embodiment, compression of the trigger arm 30 advances the rack 202 and rod 204 from the first position to the second position and compresses the actuator spring 206. The rack and pinion design and the length of the trigger arm 30 provides a mechanical advantage to overcome the bias of a trigger spring, such as a torsion spring 230, and the actuator spring 206. It is to be appreciated that the actuator spring may provide a compressive force or an extension force, or the spring may be replaced with other means, such a fluid force or a magnetic force, as non-limiting examples.

Figure 16:
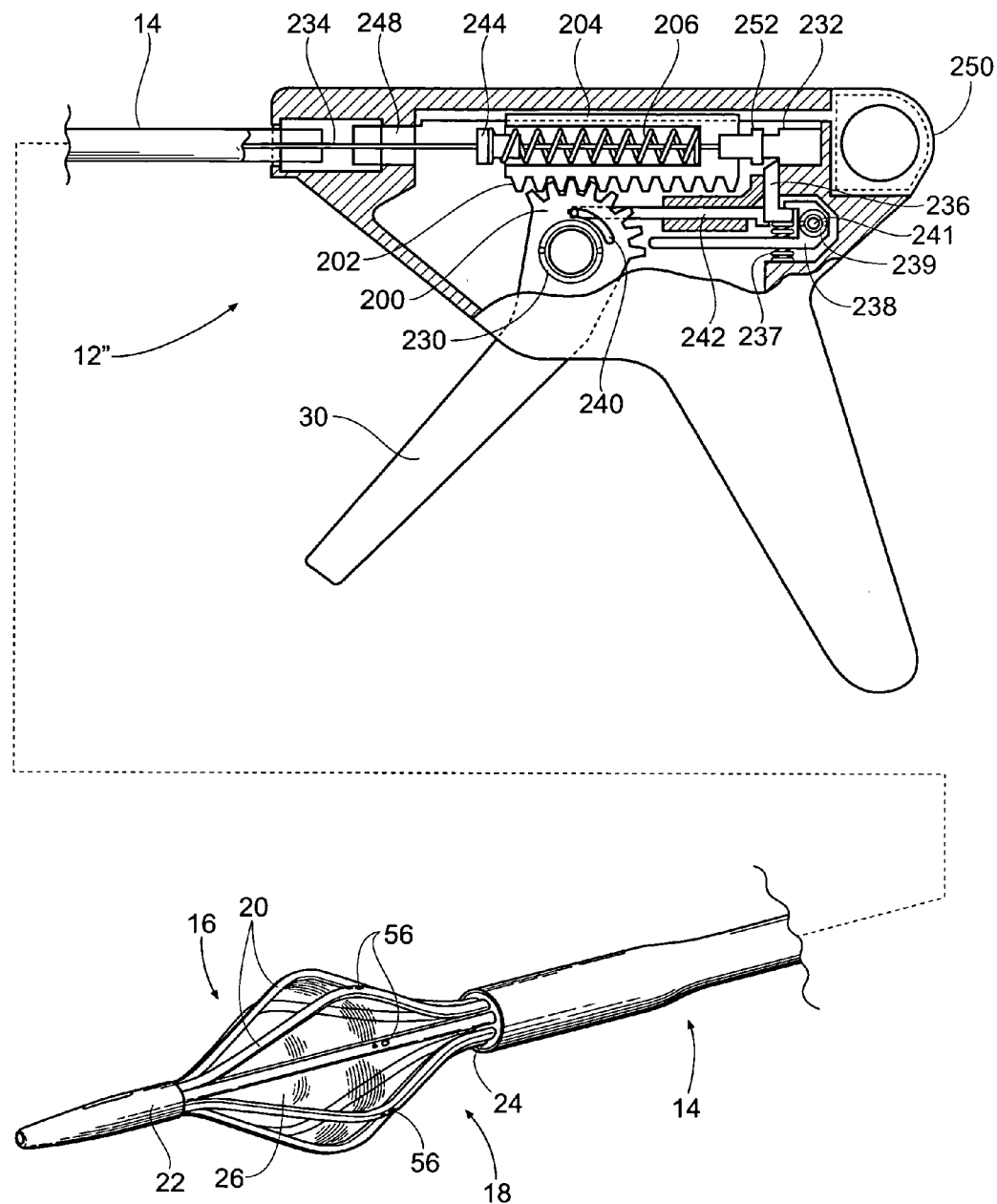
FIG. 16 is a side sectional view of an the alternative embodiment of the catheter handle shown in FIG. 15, and showing the rack and pinion trigger mechanism, the spring-loaded firing mechanism, and the retraction pull bar, and illustrating the rack in a first position and the spring-loaded firing mechanism in the battery position.

Also similar to the embodiments previously described, the handle 12" provides a sear type locking mechanism. As can be seen in FIGS. 16 and 17, a sear 232 is coupled to the proximal end of a needle or electrode advancer mandrel 234. A sear release 236, which optionally may be spring biased 237, engages the sear 232 to maintain a first position of the electrode advancer mandrel 234 until the operator moves the sear latch 238 from the first (locked) position to the second (unlocked) position to release the sear 232. The sear latch 238 may also optionally be spring biased 239 to return the sear latch to a locked or pre-firing position.

In use, with the electrodes 28 in the retracted position, the physician advances the treatment device 10 to the targeted tissue region. The physician then compresses the trigger arm 30. Cam slot 240 of trigger arm 30 moves sear release safety rod 242 distally to clear the sear release 236. A spring plunger 244 is coupled to the electrode advancer mandrel distally to the actuator spring 206. Compression of the trigger arm 30 causes the rod 204 to move from the first position to the second position, which compresses the actuator spring 206 against the spring plunger 244. The sear release 236 restricts sear 232 and spring plunger 244 from forward, or distal movement against the force of the actuator spring.

With the operators thumb, the sear latch 238 is moved downwardly, forcing sear release 236 to clear sear 232 (see FIG. 18). Once the restriction of the sear release 236 is removed from the sear 232, the stored energy of the actuator spring 206 propels the sear 232, the spring plunger 244, and the coupled electrode advancer mandrel 234 distally until the spring plunger 244 abuts the stop and electrode length adjuster 248. The electrodes 28 are now extended. The stop and electrode length adjuster 248 may be moved proximally or distally allowing for more or less travel of the spring plunger 244, which allows for more or less extension of the electrodes 28. The sear latch 238 is desirably positioned to permit single-handed compression of the trigger arm 30 and manipulation of the sear latch.

After treatment is complete and the trigger arm 30 has been released, the trigger arm may partially retract due to the biasing of the torsion spring 230. The sear release spring 237 and the sear latch spring 239 urge the sear release 236 and the sear latch 238 back to the pre-firing position. Due to possible high retraction forces, it may also be necessary to assist the retraction process by pulling on the retraction pull bar 250. During the retraction process, the distal end of the retraction pull bar engages the rod 204, causing the rack 202 and rod 204 to be returned to the first position (shown in FIG. 19) and the electrodes 28 to be retracted. The retraction process moves the rod 204 and bushing 252 proximally and will force the sear 232 to the battery position. In an alternative embodiment, the sear release 236 and the sear latch 238 may also serve to lock the electrode advancer mandrel in a second (electrode extended) position, requiring the physician to move the sear latch 238 in order to allow the retraction pull bar 250 to return the rack 202 and rod 204 to the first position.

Sear release spring 237 urges the sear release 236 back to the pre-firing position, and allows the sear release 236 to engage sear 232. The cam slot 240 of the trigger arm 30 desirably moves the sear release safety rod 242 to move under the sear release 236. The handle 12" may then be repositioned and the process repeated.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. An actuator system for deploying an electrode from a catheter assembly comprising
   a catheter assembly comprising a catheter tube and an operative element at a distal end of the catheter, said operative element comprising a basket including an array of arms, the basket movable to an expanded position,
   a handle carrying the catheter tube having a trigger lever and adapted to carry an actuator rod, the actuator rod being mechanically coupled to a plurality of electrodes each slidable within a lumen in the arms of the basket of the operative element and adapted to move the electrodes between a retracted position wherein the electrodes are contained within the operative element and an extended position wherein the electrodes extends out of the operative element, the trigger lever being actuable to deploy the electrodes prior to application of energy to the electrodes, the actuator rod movable between proximal and distal positions solely in a linear movement,
   a pinion carried by the trigger lever, and
   a rack carried by the actuator rod, the pinion engaging the rack upon compression of the trigger lever to move the rack along the actuator rod between a first position corresponding to the electrodes being in the retracted position and a second position corresponding to the electrodes being in an extended position to advance the electrodes prior to application of energy to the electrodes.

2. An actuator system as in claim 1
   wherein the actuator rod is biased in one of the first and second positions.

3. An actuator system as in claim 1, further comprising a locking element for actuator rod in at least one of the first and second positions.

4. An actuator system as in claim 3
   wherein the locking element is spring loaded.

5. An actuator system as in claim 3
   wherein the locking element is biased in a latched position.

6. An actuator system as in claim 3
   wherein at least a portion of the locking element rides along a cam surface as the rack is moved between the first and second positions.

7. An actuator system as in claim 6
   wherein the cam surface is carried by the rack.

8. An actuator system as in claim 6
   wherein the cam surface is carried by the trigger lever.

9. An actuator system as in claim 3
   wherein the rack includes a detent adapted to receive at least a portion of the locking element in at least one of the first and second positions.

10. An actuator system as in claim 3
    wherein the trigger lever includes a detent adapted to receive at least a portion of the locking element in at least one of the first and second positions.

11. The actuator assembly according to claim 1
wherein the actuator rod is mechanically coupled to the electrodes by way of an electrode advancer mandrel operating in a biased relationship to the actuator rod and further including
a locking element for locking the electrode advancer mandrel in at least one of the first and second electrode advancer mandrel positions.

12. An actuator assembly as in claim 11
wherein the locking element is spring loaded.

13. An actuator assembly as in claim 11
wherein the actuator rod is biased in one of the first and second actuator rod positions by a spring.

14. An actuator assembly as in claim 11
including a retraction member for moving the actuator rod from the second actuator rod position back to the first actuator rod position.

15. An actuator assembly as in claim 11
wherein the electrode advancer mandrel includes a sear for cooperating with the locking element.

16. An actuator assembly as in claim 15
wherein the locking element includes a sear release member for restraining and releasing the sear.

17. An actuator assembly as in claim 16
further comprising a sear latch, the sear latch being moved from a first sear latch position to a second sear latch position to move the sear release.

18. An actuator assembly as in claim 11
wherein the locking element is biased in a latched position.

19. An actuator assembly as in claim 11
further including an actuator spring, the actuator rod applying a force to the actuator spring when the actuator rod is moved from the first actuator rod position to the second actuator rod position.

20. An actuator assembly as in claim 19
wherein the locking mechanism holds the electrode advancer mandrel in at least one of the first and second electrode advancer mandrel positions against the force of the actuator spring.

21. An actuator assembly as in claim 1,
further comprising an irrigation tube extending through the handle to deliver fluid.

22. An actuator assembly as in claim 3,
wherein the locking element includes a release tab to release the locking element, the tab and trigger lever configured for single handed manipulation.

23. An actuator assembly as in claim 3,
wherein the locking element is moved to a locking position when the rack is moved to the second position.

24. An actuator assembly as in claim 3,
wherein further squeezing movement of the trigger lever releases the locking element.

* * * * *